United States Patent [19]

Carter

[11] Patent Number: 5,985,845
[45] Date of Patent: Nov. 16, 1999

[54] METHODS FOR REDUCING MORTALITY RATES IN POULTRY

[76] Inventor: A. Franklin Carter, 3001 Rockborough Ct., Ft. Collins, Colo. 80525

[21] Appl. No.: 09/234,703

[22] Filed: Jan. 21, 1999

[51] Int. Cl.$^6$ .......................... A61K 31/71; C07H 17/08

[52] U.S. Cl. ............................................. 514/31; 536/6.5

[58] Field of Search ................................ 514/31; 536/6.5; 424/180

[56] References Cited

U.S. PATENT DOCUMENTS 4,536,494  8/1985  Carter ........................................ 514/31
4,600,706  7/1986  Carter ........................................ 514/31

*Primary Examiner*—Gary L. Kunz
*Attorney, Agent, or Firm*—McDermott, Will & Emery

[57] ABSTRACT

Poultry such as chickens and turkeys are treated with natamycin to reduce overall mortality and to reduce mortality rates due to the disease ascites.

10 Claims, No Drawings

METHODS FOR REDUCING MORTALITY RATES IN POULTRY

FIELD OF THE INVENTION

This invention relates to methods for reducing mortality rates in commercially grown poultry such as chickens and turkeys, and more particularly relates to methods for the reduction of the incidence of poultry diseases such as ascites, by administration of effective amounts of a polyene such as natamycin.

BACKGROUND ART

In commercial poultry growing operations, the poultry are often subject to higher mortality rates because of the stress involved in the typical commercial raising operation. The stress is thought to be caused by the density of the poultry in the enclosure, insufficient ventilation and the presence of various diseases in the flock. In view of the crowded conditions in such commercial growing operations, any disease can be devastating to the flock which would obviously reduce the overall commercial potential of the operation.

Substantial research has been carried out to mitigate such problems and improve mortality rates of the poultry in commercial operations. The present invention provides a substantial solution to this problem.

It is also known to treat poultry feeds with various additives to prevent or inhibit certain conditions. For example, it is known from U.S. Pat. No. 4,600,706 of one of the present inventors to treat animal feed with natamycin to reduce or prevent fungal or mold growth. Similarly it is known from U.S. Pat. No. 4,536,494 of one of the inventors of the present invention that animal feed efficiency may be improved by incorporating natamycin into the animal feed.

SUMMARY OF THE INVENTION

It is accordingly one object of the present invention to provide a method for reducing the mortality rates of poultry such as chickens and turkeys in commercial growing operations.

A further object of the present invention is to provide a method for the reduction of mortality rates in commercial poultry growing operations, by specifically causing a reduction in the incidence of diseases such as ascites.

A further object of the present invention is to provide a method for the reduction of mortality, reduction of disease, and reduction of symptoms of diseases in poultry in commercial growing operations by administration thereto of effective amounts of a polyene such as natamycin.

Other objects and advantages of the present invention will become apparent as the description thereof proceeds.

In satisfaction of the foregoing objects and advantages, the present invention provides a method for reducing the mortality of poultry such as chickens and turkeys under commercial operating conditions, which comprises administration to said poultry of a polyene such as natamycin.

In still a further embodiment of the invention, the present invention provides a method for the reduction of symptoms of disease and the reduction of the incidence of diseases such as ascites in poultry by administration thereto of an effective amount of a polyene such as natamycin.

DESCRIPTION OF THE INVENTION

As noted above, the present invention is concerned with methods for reducing the mortality rates of poultry in commercial growing operations. The invention is applicable to any type of commercial poultry operation but is primarily concerned with commercial chicken and turkey growing operations. According to the present invention, it has been discovered that administration of appropriate and effective amounts of a polyene material, and especially natamycin, to poultry being grown under commercial growing operations will reduce the mortality rates in the flock and will especially reduce the presence of disease such as ascites in the poultry. It has been found according to the invention that the incidence of such diseases is lowered and mortality rates are improved in commercial chicken and turkey growing operations using the method of the invention.

It is typical in a commercial chicken and turkey growing operation that the flock is under substantial stress. As is well known, normal industry growing conditions include substantial density in the enclosure, for example, a density on the order of about 0.6 square feet per chicken or turkey. Further, the ventilation in such commercial growing operations is often not a precisely controlled operation and the determination of appropriate ventilation including both heating and cooling is a very subjective operation. Further, the life span for a broiler ranges from about 42–60 days and the life span for a turkey ranges from 12–24 weeks so that the whole operation from birth to market in conditions under which growth is achieved is very stressful to the flock. Moreover, to aggravate the problem, growers will typically push the limits of recommended industry conditions which simply increases the stress on the flock.

According to the present invention, it has been discovered that the administration of appropriate and effective amounts of a polyene such as natamycin on a regular basis to the poultry will reduce the overall mortality rate in the flock. According to the data supporting this invention, it has been found that the administration of appropriate amounts of a polyene such as natamycin will have multiple effects in curing or preventing diseases such as ascites, reducing symptoms in the flock as an apparent result of such diseases, and reducing flock mortality rates, particularly those associated with ascites.

Ascites is a disease which causes death in poultry apparently because of fluid retention. Ascites is commonly known as "water belly". There is no known cause and no apparent cure. There are theories that the amount of heat in the early days of the chicken or turkey's life, or stress, may be the cause of ascites but there is no significant data to support these theories. However, it has been found in this invention, that administration of a polyene such as natamycin has the effect of reducing the symptoms associated with ascites and also preventing death from the disease.

Natamycin is a member of the class of antibiotics known as polyenes. Polyene antibiotics have activity against yeast and fungi but no significant activity against bacteria. Nystatin, Filipin, Amphotericin B and Candicidin are also polyene antibiotics. The polyenes have molecular weights of approximately 1000 and possess large lactone rings which contain a non-polar trans conjugated double bond system and a polar polyhydroxylic system portion.

Natamycin is a creamy, white, odorless, tasteless, practically insoluble crystalline amphoteric powder. Natamycin is relatively stable when in a dry state or when mixed with dry diluents. However, the molecule is sensitive to ultra-violet light, oxygen or extreme pH values. It is relatively insoluble in water, the solubility being on the order of 10 to 100 ppm. Further even in solution, natamycin is rather unstable. Aqueous solutions may become microbiologically inactive after a 24 hour exposure to light. Natamycin is also sensitive to heavy metals and may lose up to 75% of its effectiveness in 4 or 5 hours in their presence.

Natamycin has been used to treat several human clinical fungal infections such as candidiasis and trichomoniasis. As reported in the British National Formulary, natamycin is sold under the trade name "Pimafucin®" by Gist Brocades in oral suspension, suspension for inhalation, cream and vaginal tablet formulations. Natamycin has also been used for various epidermal fungal infections such as corneal ulcers.

In none of the prior art of which applicants are aware, however, is there any suggestion that natamycin will reduce mortality rates in chickens and turkeys being grown in commercial growing operations or has any effect against bird diseases such as ascites. It is recognized that prior U.S. Pat. Nos. 4,536,494 and 4,600,706 disclose various animal and bird feed compositions which contain natamycin. The use of natamycin in the disclosures of these prior patents, however, is to improve the feed efficiency as in U.S. Pat. No. 4,536,494 or to prevent or inhibit the onset of and reduce fungal or mold growth in feed which contains moisture as in U.S. Pat. No. 4,600,706. Only very small amounts are used as described in these prior patents. There is no suggestion in these prior patents to reduce mortality or prevent or reduce diseases such as ascites by administration to birds of natamycin.

In a preferred formulation, about 2 to 25, preferably 5 to 20, grams of natamycin per pound of a carrier such as calcium carbonate is formed into a "premix". By "premix" is meant a feed composition, which, when one pound of the premix is blended with about one ton of conventional feed, the daily requirements of the natamycin are provided to the poultry for the effective treatment of ascites. A preferred formulation would contain about 10 grams natamycin to about 1 pound of calcium carbonate per ton of feed. The natamycin may be added to the carrier as a dry powder or as a liquid solution or suspension. When added as a powder, the natamycin is mixed thoroughly with the carrier to form the pre-mix. When added as a liquid, the natamycin may be dissolved or suspended in a liquid with stirring at room temperature in about five minutes by adding about 2 to 25 gm, for example, of natamycin crystals to propylene glycol or methanol, or other solvent in which natamycin will dissolve or be suspended. Because of natamycin's limited solubility, it usually will not completely go into solution, but may form a suspension. An optimal volume for suspending 2 to 25 gm of natamycin is approximately 30–60 ml. Preferably, such an amount of natamycin is then added to about one pound of a conventional premix, and will not overly wet it. The one pound of premix is then added to one ton of feed to supply daily requirements for the poultry.

Premix compositions include rice hulls which are useful because of their relatively low price. However, other premix materials may be used, including minerals such as calcium carbonate (limestone), or inerts such as soybean mill feed, or corn cob fractions. Other premix materials may be utilized, but they must be inert as are the other suggested premix materials. The natamycin solid or suspension can then be added to the premix material, and then mixed for about 10 minutes in a standard horizontal or vertical blender. In the most preferred embodiment, natamycin in a dry powder form is blended with the carrier to form the pre-mix, and the pre-mix is directly blended into feed. Alternatively, the appropriate amount of natamycin could be blended directly into the feed.

Animal feed for feeding poultry, which is a preferred feature of the invention, includes protein, fat, fiber, calcium and phosphorus. A preferred feed would include corn and/or wheat, fat, meat meal, soybean meal, minerals and vitamins.

Poultry feed is generally formed by cracking or grinding grain, rather than by incorporating the intact grain particles. These ground or cracked particles in the feed are roughly 1/100 of the original grain size. poultry feeds are composed of many different particles, typically in a range between 1/32 of an inch, or less, to 1/8 of an inch in diameter. Additionally, the cracking process exposes higher moisture and different nutrient concentrations than are typically present at the surface of the grain particle, which usually has a hull or other coating.

The premix is preferably prepared as described above and then incorporated into the feed to be fed to the poultry. There is nothing particularly special about the feed regime or the type of feed being fed to the flock. In other words, the flock is fed its usual regime so that the natamycin is being administered on a regular basis.

In a preferred embodiment of the invention, the preferred additive range of natamycin in finished feed is about 0.000055 to 0.011 weight percent (about 0.5 to 100 grams per ton of feed), preferably about 0.000055 to 0.0055 weight percent (about 0.5 to 50 grams per ton), more preferably about 0.00022 to 0.0028 weight percent (about 2 to 25 grams per ton), and most preferably about 0.00088 to 0.0017 weight percent (about 8 to 15 grams per ton). This amount of natamycin is prepared, as discussed above, and added to about one pound of premix carrier. There is no evidence that use of the higher amounts would cause any toxicity problems in treated poultry; however, the considerations of cost may become significant. Because the premix will be added to one-ton charges of feed, the correspondence between one gram of natamycin added to the premix yields about one ppm concentration of natamycin in the feed (about 0.0001 weight percent). Thus, 10 grams of natamycin added to one pound of premix, which in turn is added to a ton of feed, yields about an 11 ppm effective natamycin concentration.

Feed is conventionally prepared in a large bin or mixer in which the feed ingredients are added in descending weight order according to their prevalence in the ultimate feed mixture. Thus, cracked grain would be the primary ingredient. Minor ingredients are then added. Micro-ingredients are added last. These include vitamins, drugs, growth promoters, antibiotics, and the natamycin. Thus, natamycin can be one of the micro-ingredients and is added to the feed in the final blending step. The feed is blended for conventional time periods.

The feed comprising the natamycin is fed to flock at standard feed dosage ranges and rates. Based on the above amounts of natamycin contained in the feed, the dosage amount for each chicken or turkey per day would be about 0.0016 grams to about 0.0083 grams.

The following examples are presented to illustrate the invention but it is not to be considered as limited thereto.

EXAMPLE I

These studies involved a series of tests in commercial chicken growing operations. In these studies, chickens which were fed a diet containing a premix of 10 grams natamycin in one pound of calcium carbonate per ton of feed, were compared to other chickens which were fed a control diet composed of an identical feed that did not include the natamycin component. The studies were continued over the growth time during which time causes of each death were monitored. The following Table includes the total number of chickens in the studies, the total mortality and the cause of death attributable to the extent it could be determined.

In the following Table, the number of chickens ranges in each test from 550 to 669. It will also be noted that identical numbers of chickens were in each control group and each natamycin-treated group. The Table is as follows:

feed conversion) and mortality due to ascites. In these experiments, the natamycin was used as a 10 g/lb. premix wherein the premix was calcium carbonate. The feed level was 1 lb. natamycin/premix per ton of feed for the Treatment

TABLE I

| STUDY NUMBER | NUMBER STARTED | TOTAL MORT | NGL[1] | CU[2] | AR[3] | INJ[4] | ACT[5] | ACT-S[6] | BL[7] | DC[8] | SDS[9] | SO[10] | UNK[11] | DH[12] | BAC[13] | IE[14] | CC[15] |
|---|---|---|---|---|---|---|---|---|---|---|---|---|---|---|---|---|---|
| Exp. 1 | | | | | | | | | | | | | | | | | |
| CONTROL | 550 | 44 | 3 | 1 | 0 | 0 | 14 | 1 | 0 | 0 | 16 | 3 | 5 | 0 | 1 | 0 | 0 |
| 10 GM | 550 | 36 | 9 | 0 | 0 | 0 | 13 | 1 | 0 | 1 | 0 | 0 | 2 | 0 | 1 | 0 | 0 |
| Exp. 2 | | | | | | | | | | | | | | | | | |
| CONTROL | 550 | 53 | 7 | 3 | 0 | 0 | 24 | 0 | 1 | 1 | 12 | 1 | 2 | 0 | 0 | 0 | 0 |
| 10 GM | 550 | 46 | 5 | 1 | 0 | 0 | 16 | 2 | 0 | 0 | 16 | 0 | 4 | 0 | 2 | 0 | 0 |
| Exp. 3 | | | | | | | | | | | | | | | | | |
| CONTROL | 546 | 57 | 1 | 0 | 0 | 0 | 32 | 2 | 0 | 1 | 20 | 0 | 1 | 0 | 0 | 0 | 0 |
| 10 GM | 549 | 54 | 0 | 1 | 0 | 0 | 22 | 2 | 0 | 3 | 20 | 0 | 6 | 0 | 0 | 0 | 0 |
| Exp. 4 | | | | | | | | | | | | | | | | | |
| CONTROL | 550 | 21 | 2 | 0 | 0 | 0 | 10 | 1 | 0 | 0 | 6 | 0 | 1 | 0 | 1 | 0 | 0 |
|  | 550 | 25 | 1 | 0 | 0 | 0 | 9 | 0 | 0 | 0 | 11 |  | 1 | 0 | 3 | 0 | 0 |
| Exp. 5 | | | | | | | | | | | | | | | | | |
| CONTROL | 669 | 118 | 0 | 5 | 0 | 0 | 22 | 1 | 2 | 0 | 50 | 1 | 14 | 0 | 12 | 3 |  |
| 10 GM | 669 | 99 | 0 | 3 | 0 | 0 | 13 | 5 | 1 | 0 | 32 | 1 | 14 | 0 | 21 | 1 | 3 |
| Exp. 6 | | | | | | | | | | | | | | | | | |
| CONTROL | 578 | 42 | 0 |  | 0 | 0 | 3 | 0 | 0 | 0 | 12 | 0 | 1 | 0 |  | 8 | 17 |
| 10 GM | 580 | 35 | 0 | 1 | 0 | 0 | 4 | 1 | 0 | 0 | 8 | 0 | 3 | 0 | 2 | 1 | 15 |

[1] No growth Lesions
[2] Culls
[3] Aortic rupture
[4] Injury
[5] Ascites
[6] Ascites - sudden death
[7] Bad leg
[8] Decomposed
[9] Sudden death
[10] Starved out
[11] Unknown
[12] Dehydrated
[13] Bacterial infection
[14] Intestinal Enteritis
[15] Coccidiosis It will be noted from the Table that in a comparison of the control chickens and the natamycin-treated chickens, the total mortality was reduced from the control in Experiments 1, 2, 3 and 5. Further, a comparison of the control with the treated poultry for ascites in columns 5 and 6 (ACT and ACT-S) show a reduction in every experiment in the incidence of ascites as a cause of death to the chickens.

The data in the Table shows that there are significant differences between the results obtained with the control and natamycin-treated chickens.

The data shown in these experiments clearly shows that the administration of natamycin caused not only a reduction in ascites incidence but also an overall reduction in mortality of the chickens.

EXAMPLE II

In this example, a scientific study was carried out to create the disease symptoms in chickens and thereafter to evaluate the effects of natamycin on the disease.

In this example, a study was carried out to evaluate the effects of natamycin on broiler performance (body weights, feed conversion) and mortality due to ascites. In these experiments, the natamycin was used as a 10 g/lb. premix wherein the premix was calcium carbonate. The feed level was 1 lb. natamycin/premix per ton of feed for the Treatment 2 diets and 1½ lb. natamycin/premix per ton of feed in Treatment 3 diets. Administration was orally with the feed and administered throughout the study period.

Flavomycin was incorporated into the starter, grower and finisher diets at 2 g/ton level (fed days 0–49). Salinomycin was incorporated into the starter and grower diets at 60 g/ton level (fed days 0–42).

Normal, healthy day-old chicks were obtained from a commercial hatchery for use in this test. All birds were received from the same hatchery at the same time.

Number of birds: 1287 Males, 1287 females
Number of treatments: 3
Number of pens/treatment: 3
Number of birds/pen: 66 (33 males, 33 females)
Number of birds/treatment: 858 (429 males 429 females)
Total number of pens: 39

Treatments were assigned to pens using a complete randomized block design. Birds were assigned to the pens randomly according to CQR SOP B-10.

Specific treatments were designated as follows:

| Treatment | Description | No. of Pens | No. of Males/Pen | No. of Females/Pen | Total of Birds/Pen | Total of Birds/Treatment |
|---|---|---|---|---|---|---|
| 1 | Control | 13 | 33 | 33 | 66 | 858 |
| 2 | 1 lb/ton | 13 | 33 | 33 | 66 | 858 |
| 3 | 1½ lb/ton | 13 | 33 | 33 | 66 | 858 |
| Total | | 39 | | | | 2574 |

FEED AND ASSAYS

Ration formulations were Colorado Quality Research's standard starter, grower and finisher broiler diets. The test article and feed additives were mixed into the basal diets of the respective treatment according to the CQR SOP using a 4000-lb capacity vertical mixer. Mixed feed was stored in 50-lb capacity feed sacks and/or bulk containers. Feed was stored by treatment and treatment diets were further identified with color-codes.

After each diet had been mixed, two composite samples (~1 lb each) were collected. One sample was retained by CQR and one sample was submitted for natamycin assay. Diets were not assayed for salinomycin or flavomycin.

Assignment of treatments to pens was conducted using a computer (Excel) random numbers generator. The computer-generated assignment was as follows:

| Treatment | Pen Numbers |
|---|---|
| 1 | 2, 5, 7, 11, 14, 18, 20, 24, 30, 32, 36, 37 |
| 2 | 1, 4, 9, 12, 13, 17, 21, 22, 25, 28, 31, 34, 39 |
| 3 | 3, 6, 8, 10, 15, 16, 19, 23, 26, 29, 33, 35, 38 |

Birds were housed in concrete floor pens (~5'×9') of an environmentally controlled facility. All birds were placed in pens containing used litter. Used litter was top-dressed with approximately ~2" of clean wood shavings. Lighting was via incandescent lights and was ~23 hours continuous throughout the study.

Environmental conditions for the birds (i.e. floor space [~0.7 ft$^2$/bird], temperature, lighting, bird density, feeder and water space) was similar for all experimental groups. Ventilation was typical of the broiler industry. To help increase ascites incidence the birds were chilled for approximately 4 hours on study day 4.

Feed was provided as libitum throughout the study via two hanging, ~17-inch diameter tube feeders per pen. A chick feeder tray was also placed in each pen for approximately the first 5 days. All birds were placed on their respective treatment diets upon receipt and diets were fed continuously for 49 days at which time the study was terminated. All feed added and removed from pens was weighted and recorded. All diet changes were conducted at the same time for all pens.

Starting on day 0, any bird that was found dead or was sacrificed was weighed and recorded on the pen mortality record. All mortalities were necropsied by CQR personnel to determine the probable cause of death. Probable cause of death and necropsy findings were recorded on the pen mortality record.

Mortality data has been summarized to show the number of deaths due to ascites.

The following Table 2 shows the total mortality in the chickens over the 49 day period.

TABLE 2

| | Ascities Mortality Percent | | |
|---|---|---|---|
| | Control | 11 PPM | 16.5 PPM |
| | 15.15 | 9.09 | 9.09 |
| | 10.61 | 10.61 | 12.12 |
| | 24.24 | 15.15 | 6.06 |
| | 16.67 | 13.64 | 7.58 |
| | 13.64 | 4.55 | 7.58 |
| | 13.64 | 9.09 | 10.61 |
| | 13.64 | 9.09 | 4.55 |
| | 25.76 | 6.06 | 6.06 |
| | 18.18 | 9.09 | 6.06 |
| | 19.70 | 10.61 | 9.09 |
| | 9.09 | 4.55 | 6.06 |
| | 16.67 | 7.58 | 4.55 |
| | 13.64 | 16.67 | 4.55 |
| Average | 16.2 | 09.67*** | 7.22*** |
| SD | 4.846 | 3.739 | 2.407 |
| SEM | 1.344 | 1.037 | 0.6676 |
| P Value | | P = .0004 | P = .0001 |

***=extremely significant

As can be seen by the above table, the use of Natamycin in poultry feed as described in this invention, reduced the mortality caused by ascities by an extremely statistically significant level when compared to control birds in this experiment. This demonstrates under well controlled experimental conditions that the incorporation of natamycin in poultry feed will result in the statistically significant reduction of mortality caused by ascities.

As can be seen from the above table, total mortality due to ascites was reduced as compared to the control.

The present invention has been described herein with reference to certain preferred embodiment. However, as obvious variations thereon will become apparent to those skilled in the art, the invention is not to be considered as limited thereto.

What is claimed is:

1. A method for reducing the incidence of the disease ascites in broilers which comprises treating said broilers with an ascites-preventing effective amount of natamycin, said method comprising administering the natamycin to the broilers in broilers feed.

2. A method according to claim 1, wherein the broilers are fed on an average of one time per day a feed which comprises about 0.5 to 100 grams of natamycin per ton of feed.

3. A method according to claim 1, wherein the natamycin is administered to the feed as part of a premix which comprises an inert carrier.

4. A method according to claim 1, wherein the amount of natamycin administered to the broilers per day is about 0.0016 to about 0.0083 grams.

5. A method according to claim 3, wherein the carrier is a mineral or grain.

6. A method according to claim 3, wherein the premix is fed to the broilers by mixing with the broilers food.

7. A method according to claim 1, wherein the natamycin is administered as a mixture of natamycin and an inert carrier which is fed to the broilers by mixing with the broilers food in a ratio of about 0.5 to 50 grams of natamycin per ton of food.

8. A method according to claim 1, wherein the natamycin is administered to the broilers by daily additions of a premix of 10 grams of natamycin per pound of inert carrier to the broiler feed.

9. A method according to claim 7, wherein said inert carrier is a mineral or grain.

10. A method according to claim 9, wherein said inert carrier is calcium carbonate.

* * * * *